US012793814B2

(12) United States Patent
Ye et al.

(10) Patent No.: US 12,793,814 B2
(45) Date of Patent: Nov. 10, 2026

(54) METHOD AND APPARATUS FOR DETERMINING DRUG MOLECULE PROPERTY, AND STORAGE MEDIUM

(71) Applicant: Tencent Technology (Shenzhen) Company Limited, Shenzhen (CN)

(72) Inventors: Geyan Ye, Shenzhen (CN); Wei Liu, Shenzhen (CN); Junzhou Huang, Shenzhen (CN)

(73) Assignee: Tencent Technology (Shenzhen) Company Limited, Shenzhen (CN)

( * ) Notice: Subject to any disclaimer, the term of this patent is extended or adjusted under 35 U.S.C. 154(b) by 1107 days.

(21) Appl. No.: 17/900,583

(22) Filed: Aug. 31, 2022

(65) Prior Publication Data

US 2022/0415452 A1 Dec. 29, 2022

Related U.S. Application Data

(63) Continuation of application No. PCT/CN2021/101732, filed on Jun. 23, 2021.

(30) Foreign Application Priority Data

Jul. 30, 2020 (CN) ......................... 202010748538.6

(51) Int. Cl.
*G16C 20/30* (2019.01)
*G16C 20/50* (2019.01)
*G16C 20/70* (2019.01)

(52) U.S. Cl.
CPC ............. *G16C 20/30* (2019.02); *G16C 20/50* (2019.02); *G16C 20/70* (2019.02)

(58) Field of Classification Search
CPC ........ G16C 20/30; G16C 20/50; G16C 20/70; G06N 3/045; G06N 3/09; G06N 3/044;
(Continued)

(56) References Cited

U.S. PATENT DOCUMENTS

2004/0024772 A1* 2/2004 Itai ........................... G16B 5/00
707/999.102
2020/0164075 A1 5/2020 Chelvam et al.
(Continued)

FOREIGN PATENT DOCUMENTS

CN 103678951 A 3/2014
CN 104834831 A 8/2015
(Continued)

OTHER PUBLICATIONS

English Translation of International Search Report and Written Opinion issued Sep. 24, 2021 in International Application No. PCT/CN2021/101732 (Year: 2021).*
(Continued)

*Primary Examiner* — Mi'Schita' Henson
(74) *Attorney, Agent, or Firm* — Arent Fox Schiff LLP

(57) ABSTRACT

A method for determining a drug molecule property is provided. In the method, a text string of a drug molecule is obtained. The text string indicates a structural formula of the drug molecule. Three-dimensional structure information of the drug molecule is obtained. The three-dimensional structure information is generated according to the structural formula indicated by the text string. A drug-forming property of the drug molecule is determined based on a molecular property prediction network, the drug-forming property of the drug molecule being determined by the molecular property prediction network according to the three-dimensional structure information.

20 Claims, 9 Drawing Sheets

(58) Field of Classification Search
CPC ........ G06N 3/08; Y02D 10/00; G06F 18/214; G06V 30/40
See application file for complete search history.

(56) References Cited

U.S. PATENT DOCUMENTS

| | | | | |
|---|---|---|---|---|
| 2021/0117869 | A1* | 4/2021 | Plumbley | G06F 18/217 |
| 2023/0317202 | A1* | 10/2023 | Stojevic | G16B 15/30<br>703/12 |

FOREIGN PATENT DOCUMENTS

| | | | |
|---|---|---|---|
| CN | 106529205 | A | 3/2017 |
| CN | 109033738 | A | 12/2018 |
| CN | 106874688 | B | 3/2019 |
| CN | 110415763 | A | 11/2019 |
| CN | 111243682 | A | 6/2020 |
| CN | 111312340 | A | 6/2020 |
| CN | 111429977 | A | 7/2020 |
| CN | 111755078 | A | 10/2020 |
| JP | 2019020791 | A | 2/2019 |

OTHER PUBLICATIONS

International Search Report and Written Opinion issued Sep. 24, 2021 in International Application No. PCT/CN2021/101732 with English Translation (9 pages).
Vaswani A, Shazeer N, Parmar N, et al. Attention is all you need[C], Advances in neural information processing systems. 2017: 5998-6008.
Mauri A, Consonni V, Pavan M, et al. Dragon software: An easy approach to molecular descriptor calculations[J]. Match, 2006, 56(2): 237-248.
Rogers D, Hahn M. Extended-connectivity fingerprints[J]. Journal of chemical information and modeling, 2010, 50(5): 742-754.
Karim A, Mishra A, Newton M A H, et al. Efficient toxicity prediction via simple features using shallow neural networks and decision trees[J]. ACS Omega, 2019, 4(1): 1874-1888.
Honda S, Shi S, Ueda H R. Smiles Transformer: Pre-trained Molecular Fingerprint for Low Data Drug Discovery[J]. arXiv preprint arXiv:1911.04738, 2019.
Yang K, Swanson K, Jin W, et al. Analyzing learned molecular representations for property prediction[J]. Journal of chemical information and modeling, 2019, 59(8): 3370-3388.
Vamathevan J, Clark D, Czodrowski P, et al. Applications of machine learning in drug discovery and development[J]. Nature Reviews Drug Discovery, 2019, 18(6): 463-477.
RDKit: Open-Source Cheminformatics Software, https://www.rdkit.org/.
Halgren T A. Merck molecular force field. I. Basis, form, scope, parameterization, and performance of MMFF94[J]. Journal of computational chemistry, 1996, 17(5-6): 490-519.
Wu Z, Ramsundar B, Feinberg E N, et al. MoleculeNet: a benchmark for molecular machine learning[J]. Chemical science, 2018, 9(2): 513-530.
Vinyals O, Bengio S, Kudlur M. Order matters: Sequence to sequence for sets[J]. arXiv preprint arXiv:1511.06391, 2015.
Chinese Office Action issued Jun. 8, 2022 in Application No. 202010748538.6 with Concise English Translation (9 bages).
Yishi Fan, et al., Research on Drug Property Prediction Algorithm Based on Deep Learning, China Master's Theses Full-text Database, Medical and Health Technology Series, Jun. 15, 2020, pp. 1-61, with English Abstract.

* cited by examiner

METHOD AND APPARATUS FOR DETERMINING DRUG MOLECULE PROPERTY, AND STORAGE MEDIUM

RELATED APPLICATIONS

The present application is a continuation of International Application No. PCT/CN2021/101732, entitled "DRUG MOLECULAR PROPERTY DETERMINING METHOD AND DEVICE, AND STORAGE MEDIUM" and filed on Jun. 23, 2021, which claims priority to Chinese Patent Application No. 202010748538.6, entitled "METHOD AND APPARATUS FOR DETERMINING DRUG MOLECULE PROPERTY, AND STORAGE MEDIUM" and filed on Jul. 30, 2020. The entire disclosures of the prior applications are hereby incorporated by reference in their entirety.

FIELD OF THE TECHNOLOGY

This application relates to the field of artificial intelligence technologies, including a technology for determining a drug molecule property.

BACKGROUND OF THE DISCLOSURE

Artificial intelligence (AI) emerges in science and technology, which is researched and developed currently for simulating, extending, and expanding human intelligence. At present, the AI technology has been widely applied to many scenarios such as a drug research and development scenario.

In the drug research and development scenario, the AI technology is often used in drug molecular property prediction (MPP), also referred to as drug-forming property prediction. For example, the drug molecule property includes, but is not limited to: an absorption property, a distribution property, a metabolism property, an excretion property, and a toxicity of a drug molecule.

During drug research and development, a drug-forming property of a drug molecule is predicted, so the discovery speed of a new drug candidate can be increased, and the cost of research and development can be reduced. In other words, accurate prediction of a drug molecule property is key to increasing the discovery speed of a new drug candidate and reducing the cost of research and development.

SUMMARY

Embodiments of this disclosure include a method and apparatus for determining a drug molecule property, and a non-transitory computer-readable storage medium, which can significantly increase the prediction accuracy of the drug molecule property.

According to an aspect, a method for determining a drug molecule property is provided. In the method, a text string of a drug molecule is obtained. The text string indicates a structural formula of the drug molecule. Three-dimensional structure information of the drug molecule is obtained. The three-dimensional structure information is generated according to the structural formula indicated by the text string. A drug-forming property of the drug molecule is determined based on a molecular property prediction network, the drug-forming property of the drug molecule being determined by the molecular property prediction network according to the three-dimensional structure information.

According to another aspect, a method for training a model is provided. In the method, a training data set is obtained. The training data set includes a sample molecule and a property label associated with the sample molecule. A three-dimensional structure coordinate matrix, a normalized adjacency matrix, an atomic feature, and a chemical bond feature of the sample molecule are obtained. Feature concatenation on the three-dimensional structure coordinate matrix, the normalized adjacency matrix, the atomic feature, and the chemical bond feature of the sample molecule is performed to obtain a second concatenated matrix. A predicted property value corresponding to the sample molecule is determined according to the second concatenated matrix through an initial neural network. A loss value between the predicted property value corresponding to the sample molecule and the property label of the sample molecule is obtained based on a target loss function. Network parameters of the initial neural network are iteratively updated in response to the loss value being greater than a second threshold until the loss value is not greater than the second threshold to obtain a molecular property prediction network.

According to another aspect, an apparatus is provided. The apparatus includes processing circuitry that is configured to obtain a text string of a drug molecule, the text string indicating a structural formula of the drug molecule. The processing circuitry is configured to obtain three-dimensional structure information of the drug molecule, the three-dimensional structure information being generated according to the structural formula indicated by the text string. Further, the processing circuitry is configured to determine a drug-forming property of the drug molecule based on a molecular property prediction network, the drug-forming property of the drug molecule being determined by the molecular property prediction network according to the three-dimensional structure information.

According to another aspect, an apparatus for training a model is provided.

The apparatus includes processing circuitry that is configured to obtain a training data set, the training data set including a sample molecule and a property label associated with the sample molecule. The processing circuitry is configured to obtain a three-dimensional structure coordinate matrix, a normalized adjacency matrix, an atomic feature, and a chemical bond feature of the sample molecule. The processing circuitry is configured to perform feature concatenation on the three-dimensional structure coordinate matrix, the normalized adjacency matrix, the atomic feature, and the chemical bond feature of the sample molecule to obtain a second concatenated matrix. The processing circuitry is configured to determine a predicted property value corresponding to the sample molecule according to the second concatenated matrix through an initial neural network. The processing circuitry is configured to obtain a loss value between the predicted property value corresponding to the sample molecule and the property label of the sample molecule based on a target loss function. Further, the processing circuitry is configured to iteratively update network parameters of the initial neural network in response to the loss value being greater than a second threshold until the loss value is not greater than the second threshold to obtain a molecular property prediction network.

According to another aspect, a computer device is provided. The device includes a processor and a memory, the memory storing at least one piece of program code, the at least one piece of program code being loaded and executed by the processor to implement the method for determining a drug molecule property or the method for training a model as above.

According to another aspect, a non-transitory computer-readable storage medium is provided. The non-transitory computer-readable storage medium stores instructions which when executed by a processor cause the processor to perform any one or a combination of the methods described above.

According to another aspect, a computer program product or a computer program is provided. The computer program product or the computer program includes computer program code, the computer program code being stored in a computer-readable storage medium, a processor of a computer device reading the computer program code from the computer-readable storage medium and executing the computer program code, to cause the computer device to implement the method for determining a drug molecule property or the method for training a model as above.

The technical solutions provided in the embodiments of this disclosure include the following beneficial effects:

The embodiments of this disclosure provide a new solution for predicting a drug molecule property that is applicable in drug research and development. In this solution, when a drug molecule property is predicted, three-dimensional structure information of a to-be-tested drug molecule will be obtained. The three-dimensional structure information of the drug molecule can provide a positional distribution of each atom in the drug molecule in a three-dimensional space. A spatial structure of the drug molecule is an important factor affecting the property of the drug molecule. Therefore, based on the three-dimensional structure information of the drug molecule, the drug molecule property can be more accurately predicted, thereby increasing the discovery speed of a new drug candidate and reducing the cost of research and development.

DESCRIPTION OF EMBODIMENTS

First, some terms or abbreviations used in the embodiments of this disclosure are introduced.

The drug molecule property includes properties such as absorption, distribution, metabolism, excretion, and toxicity of a drug molecule.

Figure 1:
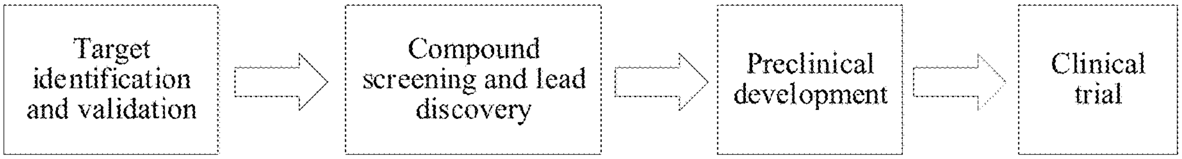
FIG. 1 is a schematic diagram of a drug research and development process according to an embodiment of this disclosure.

FIG. 1 shows a main process of drug research and development, including target identification and validation, compound screening and lead discovery, and preclinical development and clinical trial. After the target identification and validation is completed, it is necessary to screen drug candidates. In the screening process, the properties such as absorption, distribution, metabolism, excretion, and toxicity of the drug molecule may be predicted through a drug molecule property prediction algorithm, which can help developers to screen drug molecules, thereby increasing the efficiency of research and development and reducing the cost of drug research and development.

The simplified molecular input line entry specification (SMILES) is a specification for explicitly describing the structure of molecules using American Standard Code for Information Interchange (ASCII) strings. The SMILES expression can describe a three-dimensional chemical structure using a string of characters. For example, the SMILES expression of cyclohexane ($C_6H_{12}$) is C1CCCCC1, that is, C1CCCCC1 represents cyclohexane; and the SMILES expression of ethyl acetate is CC(=O)OCC, that is CC(=O)OCC represents ethyl acetate. In the related art, the drug molecule property prediction algorithm is generally used to directly predict a molecular property based on the SMILES expression of a drug candidate, but the molecular property obtained through prediction by this method usually has low accuracy.

An implementation environment involved by a solution for drug molecule property determination provided in the embodiments of this disclosure is described below.

In this specification, the drug molecule property determination is also referred to as drug molecular property prediction.

Figure 2:
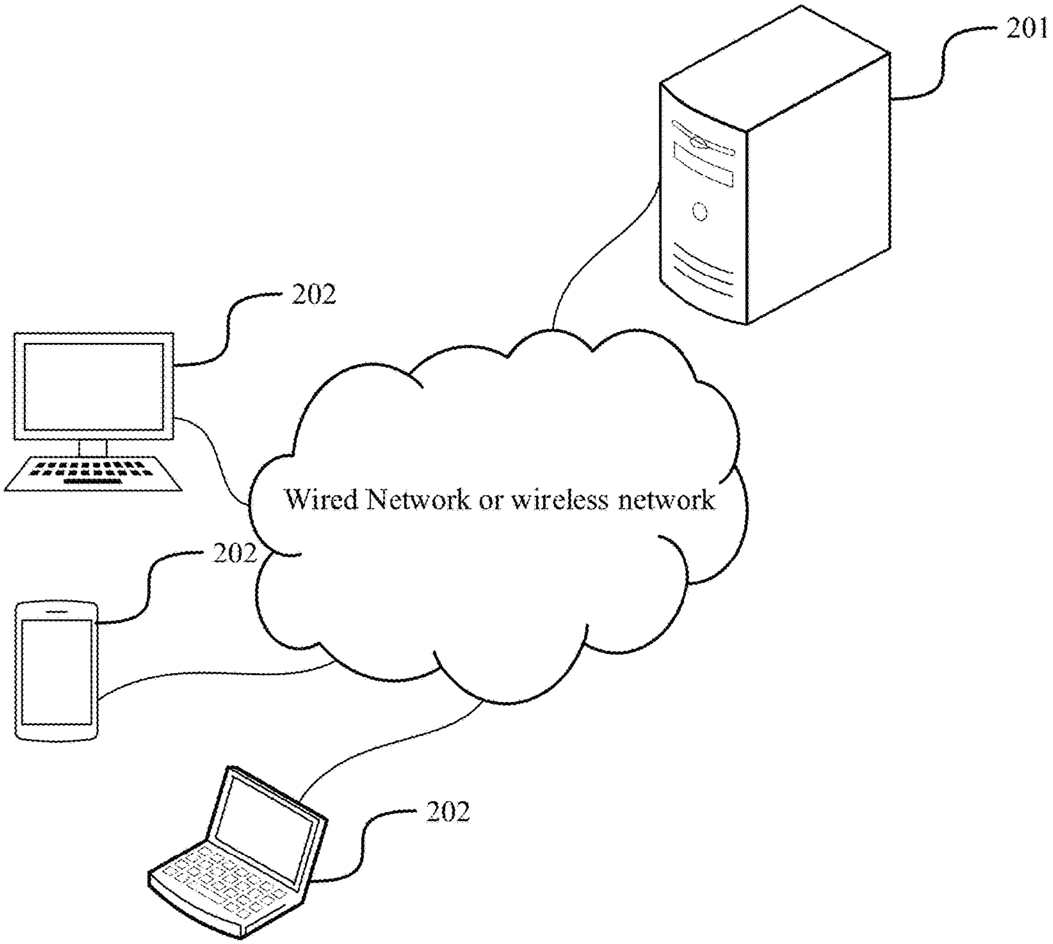
FIG. 2 is a schematic diagram of an implementation environment of a method for determining a drug molecule property according to an embodiment of this disclosure.

Referring to FIG. 2, the implementation environment includes: a first computer device 201 and a second computer device 202.

For example, the first computer device 201 may be configured to train a molecular property prediction network, and the second computer device 202 may be configured to predict a drug molecule property by using the molecular property prediction network trained by the first computer device 201. In some embodiments, the first computer device 201 and the second computer device 202 may be the same device. That is, the device may train the foregoing neural network model and then predict the drug molecule property based on the neural network model. This is not specifically limited in this embodiment of this disclosure.

In Example 1, the first computer device 201 is a server, and the second computer device 202 is a terminal.

For example, in this case, the terminal is configured with a related application. The terminal transmits the SMILES expression of a to-be-tested drug molecule through the related application to the server. The server obtains three-dimensional structure information, two-dimensional structure information, an atomic feature, and a chemical bond feature of the to-be-tested drug molecule based on the SMILES expression received, predicts a drug molecule property by using a drug molecule property prediction algorithm (that is, calling a molecular property prediction network) provided by the embodiments of this disclosure, and feeds a predicted value outputted from the molecular property prediction network back to the terminal through the related application. The terminal displays prediction results to a user.

The server may be an independent physical server, or may be a server cluster including a plurality of physical servers or a distributed system, or may be a cloud server. The terminal may be a smartphone, a tablet computer, a notebook computer, a desktop computer, a smart speaker, a smartwatch, or the like, but is not limited thereto. In addition, the terminal and the server may be directly or indirectly connected in a wired or wireless communication manner. This is not specifically limited in this disclosure.

In Example 2, the solution for predicting a drug molecule property provided in the embodiments of this disclosure may be independently completed locally by the terminal. That is, the implementation environment shown in FIG. 2 may include only the terminal.

For example, in this case, the terminal is configured with a related application. The terminal obtains three-dimensional structure information, two-dimensional structure information, an atomic feature, and a chemical bond feature of a to-be-tested drug molecule based on the SMILES expression of the to-be-tested drug molecule, predicts a drug molecule property by using a drug molecule property prediction algorithm (that is, calling a molecular property prediction network) provided by the embodiments of this disclosure, and displays prediction results to a user.

As noted above, the solution for predicting a drug molecule property provided in the embodiments of this disclosure may be executed jointly by the terminal and the server, or may be executed independently by the terminal, or may be executed independently by the server. The computer device configured to execute the solution for predicting a drug molecule property is not specifically limited in the embodiments of this disclosure.

Based on the foregoing implementation environment, the solution for predicting a drug molecule property provided in the embodiments of this disclosure includes: introducing a Transformer model in the field of natural language processing, and predicting a molecular property based on molecular three-dimensional structure information. In other words, in this technical solution, according to an aspect, the three-dimensional structure information of a molecule is introduced, and a data argumentation (DA) method based on the three-dimensional structure information of the molecule is provided, so that the accuracy of molecular property prediction is increased; according to another aspect, the Transformer model in the field of natural language processing is introduced, and a new method for applying the Transformer model in the field of molecular property prediction is provided, so that the accuracy of molecular property prediction is further increased due to a powerful expressive capability of the Transformer model.

The solution for predicting a drug molecule property provided in the embodiments of this disclosure may be used in the process of drug research and development to predict a drug-forming property of a drug molecule, so that the discovery speed of a new drug candidate is increased, and the cost of research and development is reduced.

The solution for predicting a drug molecule property provided in the embodiments of this disclosure is described in detail below by using the following embodiments.

Figure 3:
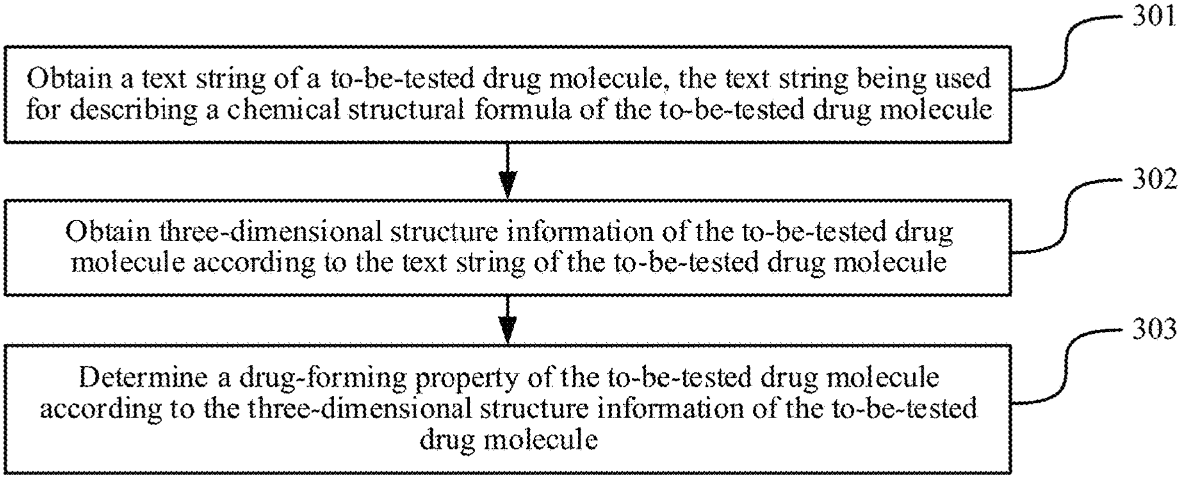
FIG. 3 is a flowchart of a method for determining a drug molecule property according to an embodiment of this disclosure.

FIG. 3 is a flowchart of a method for determining a drug molecule property according to an embodiment of this disclosure. The method is performed by a computer device. For example, the computer device may include only a terminal, or may include only a server, or may include a terminal and a server. Referring to FIG. 3, a method process provided in this embodiment of this disclosure includes the following steps.

In step 301, a text string of a to-be-tested drug molecule is obtained, the text string being used for describing a chemical structural formula of the to-be-tested drug molecule.

In this embodiment of this disclosure, the to-be-tested drug molecule refers to a drug molecule with a molecular property to be predicted.

For example, the text string refers to a SMILES expression. The SMILES expression can describe a three-dimensional chemical structure using a string of characters and can transform a chemical structure of a molecule into a spanning tree. During the transformation, it is usually necessary to remove a hydrogen atom and open a ring. During the expression, the atom removed at an end of a bond usually needs to be numbered, and a branch is written in parentheses.

In summary, the transformation rules are as follows: omit the hydrogen atom, do not express a single bond but write adjacent atoms to be next to each other, express a double bond with =, express a triple bond with #, resolve a chemical structural formula as one chain, and write a side chain in parentheses to be next to an attached atom.

In step 302, three-dimensional structure information of the to-be-tested drug molecule is obtained according to the text string of the to-be-tested drug molecule.

The embodiments of this disclosure provide a DA method based on the three-dimensional structure information of the drug molecule. For example, the three-dimensional structure information of the to-be-tested drug molecule is three-dimensional structure coordinates of the to-be-tested drug molecule.

In sub-step 302-1. Obtain three-dimensional structure coordinates of the to-be-tested drug molecule are obtained according to the text string of the to-be-tested drug molecule.

As an example, in the embodiments of this disclosure, three-dimensional structure coordinates (x,y,z) of each atom in the to-be-tested drug molecule may be obtained through the software RDKit as follows. That is, the obtaining three-dimensional structure coordinates of the to-be-tested drug molecule according to the text string includes the following steps.

Step a. Obtain the chemical structural formula of the to-be-tested drug molecule according to the text string of the to-be-tested drug molecule.

In this step, based on the SMILES expression of the to-be-tested drug molecule, according to an inverse process of the transformation rules introduced in step 301, the molecular representation of the to-be-tested drug molecule is obtained, and the hydrogen atom is supplemented.

Step b. Determine M three-dimensional structures with different conformers according to the chemical structural formula of the to-be-tested drug molecule.

For example, M is 10, that is, three-dimensional structures with 10 different conformers are obtained. A spatial conformer of a molecule refers to a geometric shape of various groups or atoms distributed in a space of the molecule. Atoms in a molecule are not piled up disorderly, but are bound into a whole according to a specific rule, so that the molecule presents a specific geometric shape (that is, a conformer) in the space.

In a possible implementation, in order to avoid the generation of very similar conformers, two three-dimensional structures with different conformers also need to satisfy the following condition: a root mean squared error (RMSE) is greater than a first threshold. The first threshold may be 0.5 Å. This is not specifically limited in this embodiment of this disclosure.

Step c. Perform energy minimization on the M three-dimensional structures respectively under a target molecular force field.

As an example, the target molecular force field is Merck molecular force field 94 (MMFF94). This is not specifically limited in this embodiment of this disclosure.

For example, M is 10, in this embodiment of this disclosure, force field optimization is performed on the three-dimensional structures with 10 different conformers obtained in step b by using MMFF94. That is, energy minimization is performed on the three-dimensional structures with different conformers by using MMFF94.

Step d. Determine a three-dimensional structure with a minimum energy from the M three-dimensional structures as a target three-dimensional structure; and remove a hydrogen atom from the target three-dimensional structure to obtain a three-dimensional structure of the to-be-tested drug molecule.

For example, M is 10, in this embodiment of this disclosure, a three-dimensional structure with a minimum energy (referred to as a target three-dimensional structure herein) is selected from the optimized three-dimensional structures with 10 conformers as the three-dimensional structure of the to-be-tested drug molecule, and the hydrogen atom therein is removed.

Step e. Obtain three-dimensional coordinates of each atom in the to-be-tested drug molecule under the three-dimensional structure of the to-be-tested drug molecule to obtain the three-dimensional structure coordinates of the to-be-tested drug molecule.

After the three-dimensional structure coordinates of the to-be-tested drug molecule are obtained, in order to achieve data argumentation, step 302-2 is also included as follows before the coordinates are inputted to a neural network model.

In sub-step 302-2, transformation is performed on the three-dimensional structure coordinates of the to-be-tested drug molecule when a three-dimensional structure shape of the to-be-tested drug molecule remains unchanged, to obtain a three-dimensional structure coordinate matrix of the to-be-tested drug molecule.

For example, the transformation includes, but is not limited to, random rotation and translation.

Correspondingly, performing transformation on the current three-dimensional structure coordinates of the to-be-tested drug molecule includes:

obtaining a random rotation matrix and a translation transformation matrix; and performing, when the three-dimensional structure shape of the to-be-tested drug molecule remains unchanged, random rotation and translation transformation on a three-dimensional structure of the to-be-tested drug molecule respectively according to the random rotation matrix and the translation transformation matrix to obtain the three-dimensional structure coordinate matrix, the three-dimensional structure coordinate matrix including new three-dimensional structure coordinates of the to-be-tested drug molecule.

In other words, in this step, random rotation and translation are performed on the three-dimensional structure determined in sub-step 302-1 by using the random rotation matrix and the translation matrix, and the three-dimensional structure shape of the to-be-tested drug molecule is ensured to remain unchanged.

Figure 4:
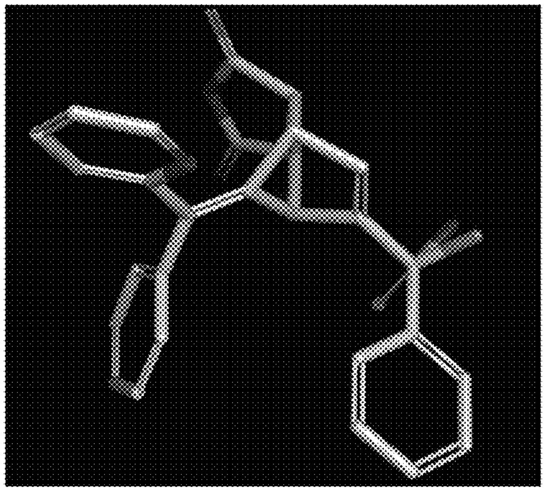
FIG. 4 is a diagram of a three-dimensional structure of a molecule according to an embodiment of this disclosure.
Figure 5:
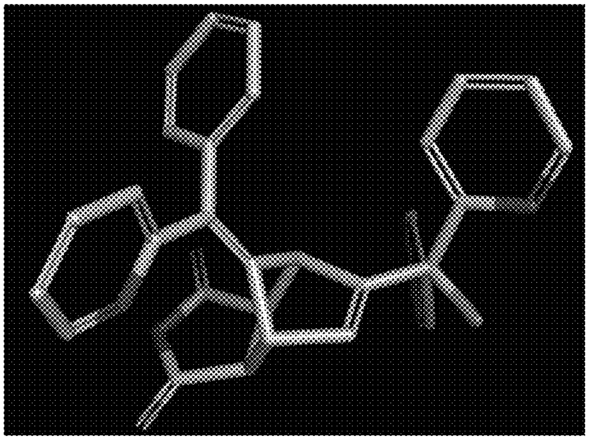
FIG. 5 is a diagram of a three-dimensional structure obtained after random rotation and translation transformation of the three-dimensional structure shown in FIG. 4.

FIG. 4 shows a three-dimensional structure of norbormide ($C_{33}H_{25}N_3O_3$). The three-dimensional structure is subjected to random rotation and translation to obtain the result shown in FIG. 5. Comparing FIG. 4 and FIG. 5, it can be recognized that the three-dimensional structure coordinates of the molecule have changed, but the three-dimensional structure shape of the molecule remains unchanged.

In step 303, a drug-forming property of the to-be-tested drug molecule is determined according to the three-dimensional structure information of the to-be-tested drug molecule.

In a possible implementation, the three-dimensional structure information of the to-be-tested drug molecule may be inputted to the molecular property prediction network, and the drug-forming property of the to-be-tested drug molecule may be determined by calling the molecular property prediction network.

That is, the determining a drug-forming property of the to-be-tested drug molecule according to the three-dimensional structure information includes the following steps.

Input the three-dimensional structure coordinate matrix of the to-be-tested drug molecule to the molecular property prediction network to obtain a predicted property value outputted from the molecular property prediction network, the predicted property value outputted being used for indicating the drug-forming property of the to-be-tested drug molecule.

The embodiments of this disclosure provide a solution for predicting a drug molecule property that is applicable in drug research and development. In this solution, when a drug molecule property is predicted, three-dimensional structure information of a to-be-tested drug molecule will be obtained. The three-dimensional structure information of the drug molecule can provide a positional distribution of each atom in the drug molecule in a three-dimensional space. A spatial structure of the drug molecule can affect the property of the drug molecule. Therefore, based on the three-dimensional structure information of the drug molecule, the drug molecule property can be accurately predicted, thereby increasing the discovery speed of a new drug candidate and reducing the cost of research and development.

In an embodiment, when the drug-forming property of the to-be-tested drug molecule is predicted, in addition to obtaining the three-dimensional structure information of the to-be-tested drug molecule through sub-steps 302-1 and 302-2, two-dimensional structure information of the to-be-tested drug molecule may also be obtained. For example, the two-dimensional structure information is an adjacency matrix of a two-dimensional structure diagram of the molecule. That is, step 302 further includes: obtaining two-dimensional structure information of the to-be-tested drug molecule according to the text string of the to-be-tested drug molecule.

In sub-step 302-3, an adjacency matrix corresponding to a two-dimensional structure diagram of the to-be-tested drug molecule is obtained according to the text string of the to-be-tested drug molecule; and normalization on the adjacency matrix corresponding to the two-dimensional structure diagram of the to-be-tested drug molecule is performed to obtain a normalized adjacency matrix of the to-be-tested drug molecule.

For example, the SMILES expression may be imported and converted into a two-dimensional structure diagram by most molecule editing software. The SMILES expression may be converted into the two-dimensional structure diagram by using structure diagram generation algorithms (SDGAs). This is not specifically limited in this embodiment of this disclosure.

In a possible implementation, the performing normalization on the adjacency matrix corresponding to the two-dimensional structure diagram to obtain a normalized adjacency matrix includes: transforming a value of a diagonal element of the adjacency matrix from a first numerical value to a second numerical value to obtain a new adjacency matrix; and performing normalization on the new adjacency matrix to obtain the normalized adjacency matrix. The first numerical value may be 0, and the second numerical value may be 1. This is not specifically limited in this embodiment of this disclosure.

Figure 6:
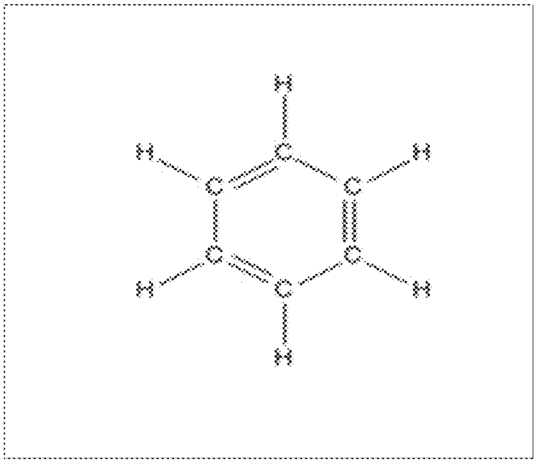
FIG. 6 is a two-dimensional structure diagram of a benzene ring according to an embodiment of this disclosure.

In an example, a benzene ring (SMILES: c1ccccc1) is used. FIG. 6 shows a two-dimensional structure of the benzene ring including six carbon atoms and an adjacency matrix as follows:

$$\begin{bmatrix} 0 & 1 & 0 & 0 & 0 & 1 \\ 1 & 0 & 1 & 0 & 0 & 0 \\ 0 & 1 & 0 & 1 & 0 & 0 \\ 0 & 0 & 1 & 0 & 1 & 0 \\ 0 & 0 & 0 & 1 & 0 & 1 \\ 1 & 0 & 0 & 0 & 1 & 0 \end{bmatrix}$$

Based on the adjacency matrix plus self-binding of atoms (the atoms themselves are also bound with each other), diagonal elements of the adjacency matrix are changed from 0 to 1 to obtain the following matrix (the left matrix). Finally, for convenience of data processing, rows of the foregoing matrix are normalized to obtain the normalized adjacency matrix. For example, the normalization is to convert each matrix element into a decimal between 0 and 1. The normalized adjacency matrix is shown as the following right matrix.

$$\begin{bmatrix} 1 & 1 & 0 & 0 & 0 & 1 \\ 1 & 1 & 1 & 0 & 0 & 0 \\ 0 & 1 & 1 & 1 & 0 & 0 \\ 0 & 0 & 1 & 1 & 1 & 0 \\ 0 & 0 & 0 & 1 & 1 & 1 \\ 1 & 0 & 0 & 0 & 1 & 1 \end{bmatrix} \begin{bmatrix} \frac{1}{3} & \frac{1}{3} & 0 & 0 & 0 & \frac{1}{3} \\ \frac{1}{3} & \frac{1}{3} & \frac{1}{3} & 0 & 0 & 0 \\ 0 & \frac{1}{3} & \frac{1}{3} & \frac{1}{3} & 0 & 0 \\ 0 & 0 & \frac{1}{3} & \frac{1}{3} & \frac{1}{3} & 0 \\ 0 & 0 & 0 & \frac{1}{3} & \frac{1}{3} & \frac{1}{3} \\ \frac{1}{3} & 0 & 0 & 0 & \frac{1}{3} & \frac{1}{3} \end{bmatrix}$$

In another embodiment, when the drug-forming property of the to-be-tested drug molecule is predicted, in addition to obtaining the three-dimensional structure information of the to-be-tested drug molecule through sub-steps 3021 and 3022, an atomic feature and a chemical bond feature of the to-be-tested drug molecule may also be obtained. That is, step 302 further includes the following steps.

In sub-step 302-4, an atomic feature and a chemical bond feature of the to-be-tested drug molecule are obtained according to the text string of the to-be-tested drug molecule.

In this step, the atomic feature and the chemical bond feature of the to-be-tested drug molecule may be obtained according to the text string of the to-be-tested drug molecule through the Rdkit software. This is not specifically limited in this embodiment of this disclosure.

It is to be understood that in actual application, in this embodiment of this disclosure, only sub-step 302-3 may be performed, or only sub-step 302-4 may be performed, or sub-step 302-3 and sub-step 302-4 may be performed in a sequence or at the same time. When only sub-step 302-3 is performed, step 303 may be replaced with: determining the drug-forming property of the to-be-tested drug molecule according to the three-dimensional structure information and the two-dimensional structure information of the to-be-tested drug molecule. When only sub-step 302-4 is performed, step 303 may be replaced with: determining the drug-forming property of the to-be-tested drug molecule according to the three-dimensional structure information, the atomic feature, and the chemical bond feature of the to-be-tested drug molecule. When sub-steps 302-3 and step 302-4 are performed in a sequence or at the same time, step 303 may be replaced with: determining the drug-forming property of the to-be-tested drug molecule according to the three-dimensional structure information, the two-dimensional structure information, the atomic feature, and the chemical bond feature of the to-be-tested drug molecule.

For example, step 303 is replaced with "determining the drug-forming property of the to-be-tested drug molecule according to the three-dimensional structure information, the two-dimensional structure information, the atomic feature, and the chemical bond feature of the to-be-tested drug molecule", and the following introduces a specific implementation of this step. It is to be understood that other replacement forms have a specific implementation similar to this replacement form, which can be implemented by a person skilled in the art using similar technical means.

In a possible implementation, the three-dimensional structure information, the two-dimensional structure information, the atomic feature, and the chemical bond feature of the to-be-tested drug molecule are inputted to the molecular property prediction network, and the drug-forming property of the to-be-tested drug molecule may be determined by calling the molecular property prediction network. That is, the determining the drug-forming property of the to-be-tested drug molecule according to the three-dimensional structure information, the two-dimensional structure information, the atomic feature, and the chemical bond feature including the following steps.

In sub-step 303-1, feature concatenation is performed on the three-dimensional structure coordinate matrix, the normalized adjacency matrix, the atomic feature, and the chemical bond feature of the to-be-tested drug molecule to obtain a first concatenated matrix.

The feature concatenation may be performed by using the concat function. This is not specifically limited in this embodiment of this disclosure. The concatenated matrix obtained herein is also referred to as the first concatenated matrix.

In sub-step 303-2, a predicted property value is determined according to the first concatenated matrix of the to-be-tested drug molecule through a molecular property prediction network, the predicted property value being used for indicating the drug-forming property of the to-be-tested drug molecule.

For example, the drug-forming property of the drug molecule includes, but is not limited to, absorption, distribution, metabolism, excretion, toxicity, and the like. The predicted property value outputted from the molecular property prediction network may include a predicted value of each drug-forming property of the to-be-tested drug molecule. Assuming that a property value of each drug-forming property ranges from 0 to 10, using toxicity as an example, 0 means no toxicity, and 10 means the highest toxicity.

Figure 7:
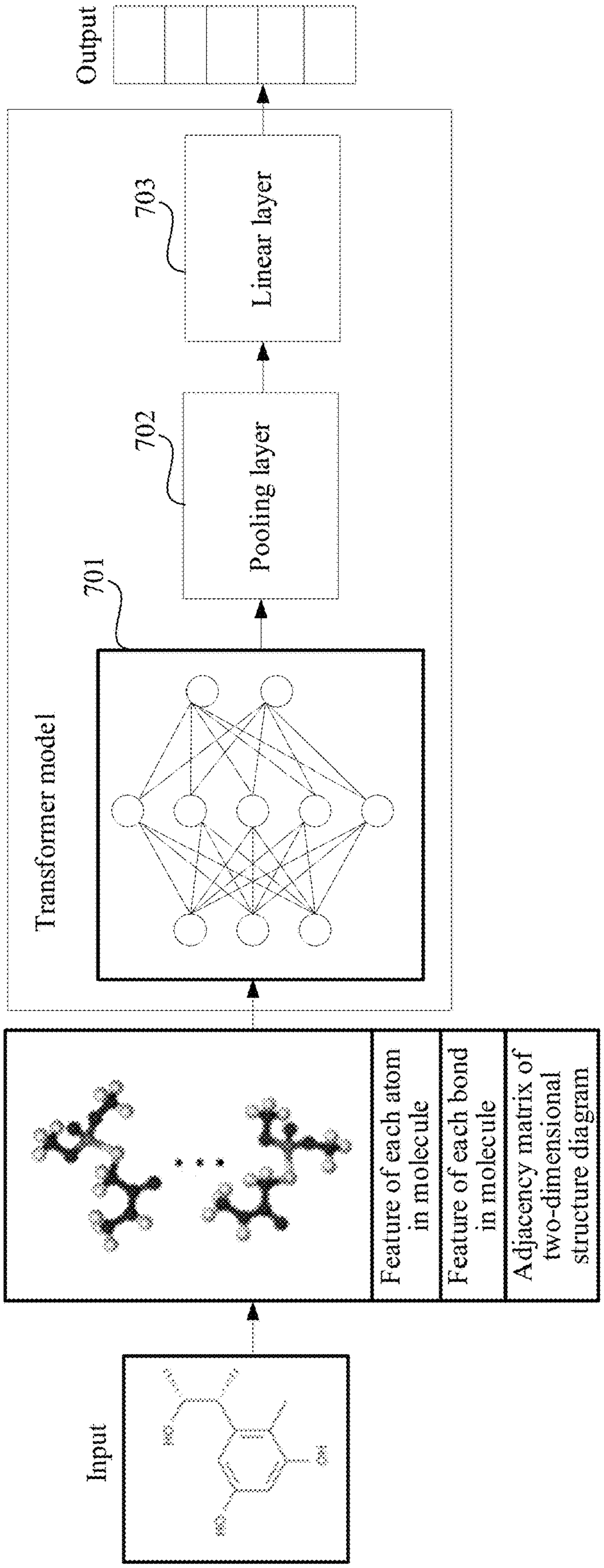
FIG. 7 is a flowchart of a method for determining a drug molecule property according to an embodiment of this disclosure.

FIG. 7 shows a possible structure of the molecular property prediction network. Referring to FIG. 7, the molecular property prediction network includes a feature encoding layer 701, a pooling layer 702, and a linear layer 703.

For example, the feature encoding layer 701 introduces the Transformer model in the field of natural language processing. That is, this embodiment of this disclosure provides a new method for applying the Transformer model in the field of molecular property prediction. In this embodiment of this disclosure, the three-dimensional structure information, the two-dimensional structure information, the atomic feature, and the chemical bond feature of the to-be-tested drug molecule are obtained, and the features are concatenated as an input of the feature encoding layer 701. This method can greatly increase the accuracy of predicting the molecular property.

In a possible implementation, the pooling layer 702 may be an average pooling layer, and the linear layer 703 may include a plurality of linear layers. This is not specifically limited in this embodiment of this disclosure.

For example, the three-dimensional structure coordinates, the normalized adjacency matrix, the atomic feature, and the chemical bond feature of the to-be-tested drug molecule are concatenated and then inputted to the molecular property prediction network, and atomic code of the to-be-tested drug molecule will be obtained after the input data is encoded by the feature encoding layer 701 of the molecular property prediction network (an atom-surrounding bond feature has been already encoded on the atomic code by the molecular property prediction network).

The embodiments of this disclosure provide a solution for predicting a drug molecule property that is applicable in drug research and development. In this solution, when a drug molecule property is predicted, three-dimensional structure information, two-dimensional structure information, an atomic feature, and a chemical bond feature of a to-be-tested drug molecule will be obtained. The obtaining of various information can help accurately predict the drug molecule property, thereby increasing the discovery speed of a new drug candidate and reducing the cost of research and development. In addition, the embodiments of this disclosure also introduce the Transformer model in the field of natural language processing, and provide a new method for applying the Transformer model in the field of molecular property prediction, so that the accuracy of molecular property is further increased due to a powerful expressive capability of the Transformer model.

Figure 8:
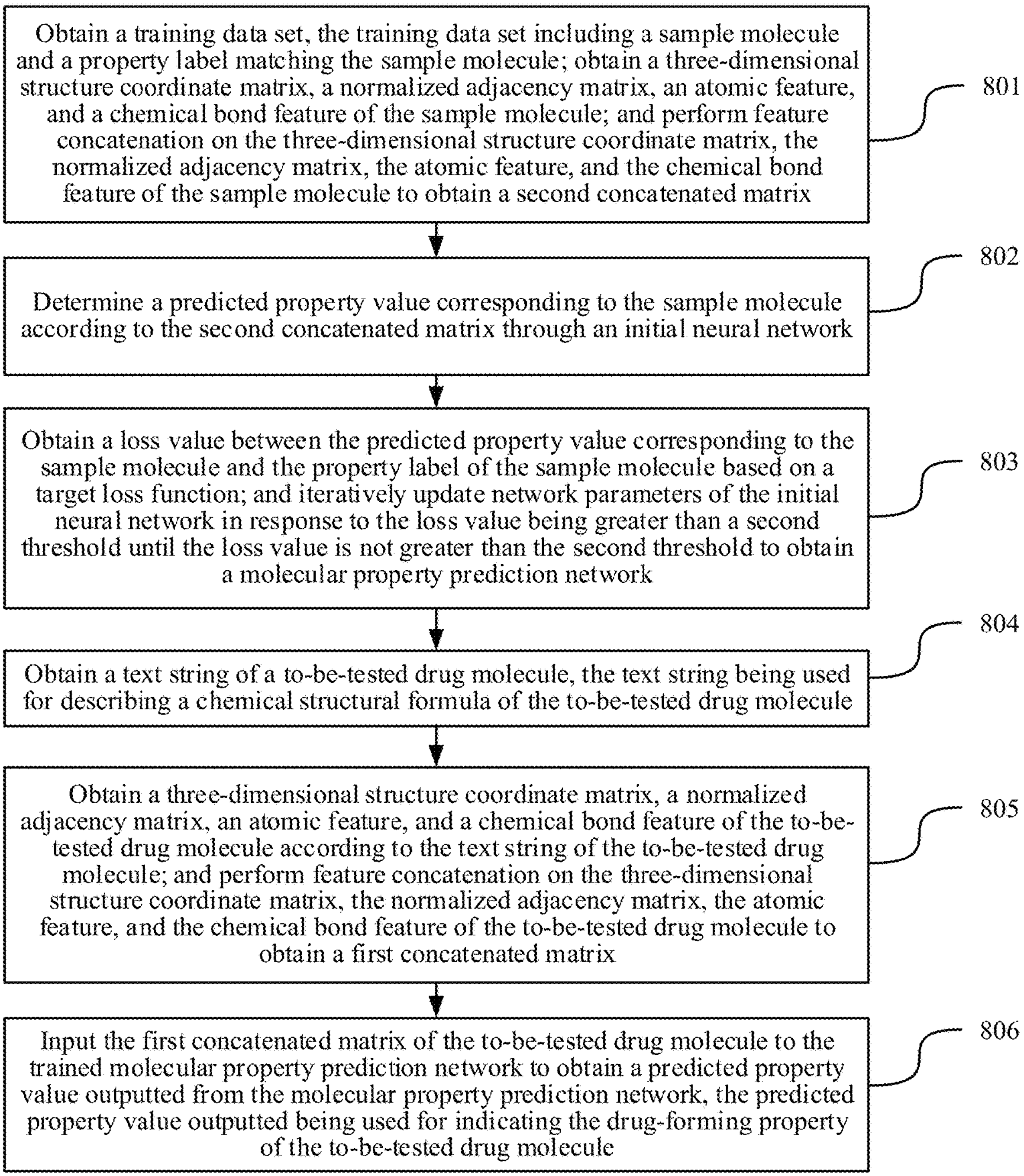
FIG. 8 is a schematic structural diagram of a molecular property prediction network according to an embodiment of this disclosure.

FIG. 8 is a flowchart of a method for determining a drug molecule property according to an embodiment of this disclosure. The method is performed by a computer device. For example, the computer device may include only a terminal, or may include only a server, or may include a terminal and a server. Aiming at the problem of drug molecule property prediction during drug research and development, the embodiments of this disclosure provide a solution for predicting a drug molecule property, which can efficiently predict drug molecule properties ADMET (such as absorption, distribution, metabolism, excretion, and toxicity), and help drug developers to screen and design drug molecules. Referring to FIG. 8, a method process provided in this embodiment of this disclosure includes the following steps.

In step 801, obtain a training data set, the training data set including a sample molecule and a property label matching the sample molecule; obtain a three-dimensional structure coordinate matrix, a normalized adjacency matrix, an atomic feature, and a chemical bond feature of the sample molecule; and perform feature concatenation on the three-dimensional structure coordinate matrix, the normalized adjacency matrix, the atomic feature, and the chemical bond feature of the sample molecule to obtain a second concatenated matrix.

This step may be performed with reference to step 302. Details are not described herein again.

In step 802, determine a predicted property value corresponding to the sample molecule is determined according to the second concatenated matrix through an initial neural network.

The predicted property value corresponding to the sample molecule is a result obtained through prediction by the initial neural network to be trained according to the second concatenated matrix. The property label of the sample molecule is a true value of a drug-forming property of the sample molecule.

In combination with FIG. 7, it can be recognized that in the solution for predicting a drug molecule property, a feed forward process of model training includes the following steps.

In sub-step 802-1, obtain a three-dimensional structure coordinate matrix of the sample molecule, a feature of each atom in the sample molecule, a feature of each chemical bond in the sample molecule, and an adjacency matrix corresponding to a two-dimensional structure diagram of the sample molecule according to the SMILES expression of the sample molecule.

In sub-step 802-2, perform random rotation and translation transformation on a three-dimensional structure of the sample molecule to achieve data argumentation; perform normalization on the adjacency matrix corresponding to the two-dimensional structure diagram of the sample molecule; and perform feature concatenation on the three-dimensional structure coordinate matrix, the adjacency matrix of the two-dimensional structure diagram, the feature of each atom in the sample molecule, and the feature of each chemical bond in the sample molecule that are processed.

In sub-step 802-3, input the concatenated matrix (herein referred to as the second concatenated matrix) as input data of a neural network model to the neural network model, and obtain an encoded vector of the sample molecule through the feature encoding layer 701 and the pooling layer 702 in the neural network model.

The neural network model involved in this step is the initial neural network involved in step 802.

In sub-step 802-4, obtain a final output of the neural network model from the encoded vector of the sample molecule through the linear layer 703, an output value being the predicted property value of the drug-forming property of the sample molecule.

In step 803, obtain a loss value between the predicted property value outputted from the initial neural network and the property label of the sample molecule based on a target loss function; and iteratively update network parameters of the initial neural network in response to the loss value being greater than a second threshold until the loss value is not greater than the second threshold to obtain a molecular property prediction network.

During model training, a loss function is usually used to determine whether the model converges. The loss function may be a cross-entropy loss function. This is not specifically limited in this embodiment of this disclosure. Usually, the loss function is used for calculating a degree of difference between the predicted value outputted by the model and the property label, that is, the loss value.

Whether the predicted value outputted by the model matches the property label is determined based on the loss function. For example, when the degree of difference between the predicted value and the property label is less than the second threshold, it is considered that the predicted value matches the property label, and the training ends. Alternatively, when the number of training iterations reaches a preset number, the training ends. This is not specifically limited in this embodiment of this disclosure.

For example, in this embodiment of this disclosure, the predicted value of the drug-forming property of the sample molecule obtained through feed forward calculation and the true value are compared to obtain a loss value as a loss function of the neural network model, a gradient of each network layer is calculated during back forward calculation, and the network parameters of the neural network model are updated by using an Adaptive Moment Estimation (Adam) algorithm.

Figure 9:
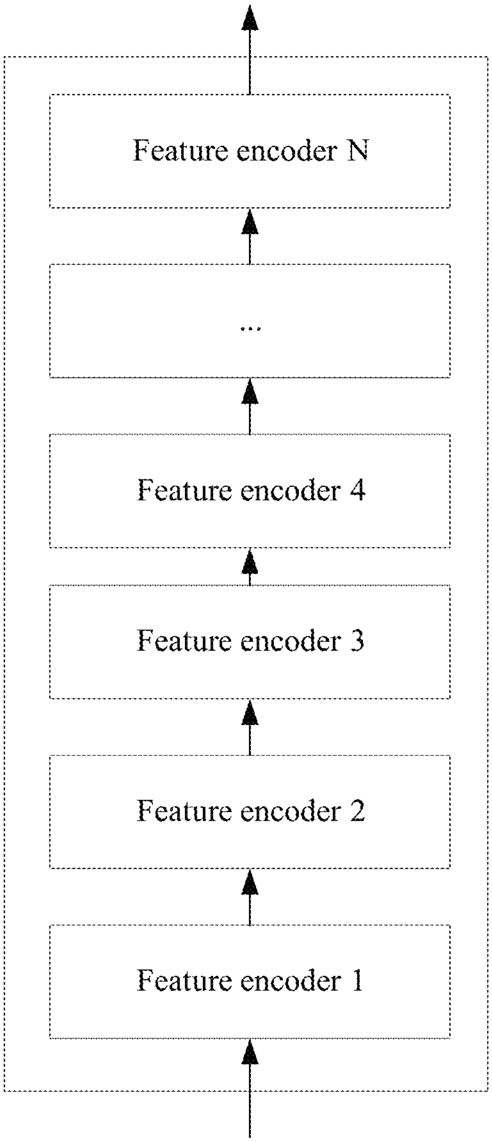
FIG. 9 is a schematic structural diagram of a feature encoding layer according to an embodiment of this disclosure.

As an example, in this embodiment of this disclosure, the Encoder (encoding module) portion of the Transformer model is used in the feature encoding layer 701 portion. The structure of Encoder is shown in FIG. 9.

That is, Encoder includes N layers of feature encoders with the same structure that are sequentially stacked, N being a positive integer. During feature encoding, this embodiment of this disclosure includes: inputting the second concatenated matrix as an input feature to a first layer of feature encoder of Encoder; encoding the input feature sequentially through the N layers of feature encoders stacked until a last layer of feature encoder, an output of a previous layer of feature encoder being used as an input of a next layer of feature encoder; and determining an output of the last layer of feature encoder as an output feature of Encoder.

In another possible implementation, an attention mechanism may be combined into a natural language processing task. The network model combined with the attention mechanism pays great attention to feature information of a specific target during training, and can effectively adjust the network parameters for different targets and mine more hidden feature information.

The attention mechanism has two main aspects: deciding which part of an input needs attention; and allocating limited information processing resources to an important part. The attention mechanism in deep learning is essentially similar to the human selective visual attention mechanism, and the core target is also to select information that is more critical to the current task from a large number of information.

As an example, each layer of feature encoder includes a multi-head attention layer and a feedforward neural network layer. That is, the feature encoder uses a multi-head attention mechanism. Correspondingly, the encoding the input feature sequentially through the N layers of feature encoders stacked includes the following steps.

In sub-step 803-1, Obtain, when a $j^{th}$ layer of feature encoder includes an $i^{th}$ head structure of the multi-head attention layer, a first linear transformation matrix, a second linear transformation matrix, and a third linear transformation matrix corresponding to the $i^{th}$ head structure, both i and j being positive integers, $1 \leq j \leq N$.

In this specification, the first linear transformation matrix, the second linear transformation matrix, and the third linear transformation matrix may be represented by symbols $W_i^Q$, $W_i^K$, and $W_i^V$ respectively.

In sub-step 803-2, perform linear transformation on an input feature of the $i^{th}$ head structure respectively according to the first linear transformation matrix, the second linear transformation matrix, and the third linear transformation matrix to obtain a query sequence, a key sequence, and a value sequence of the $i^{th}$ head structure sequentially; and obtain an output feature of the $i^{th}$ head structure according to the query sequence, the key sequence, and the value sequence of the $i^{th}$ head structure.

First, the input feature of the $i^{th}$ head structure is matrix-multiplied by $W_i^Q$, $W_i^K$, and $W_i^V$ respectively to obtain the query sequence $Q_i$, the key sequence $K_i$, and the value sequence $V_i$ of the $i^{th}$ head structure.

Then, the output feature $Z_i$ of the $i^{th}$ head structure is calculated based on the query sequence $Q_i$, the key sequence $K_i$, and the value sequence $V_i$ of the $i^{th}$ head structure.

$$Z_i = \mathrm{softmax}\left(\frac{Q_i K_i^T}{\sqrt{d_k}}\right)V_i,$$

and $d_k$ refers to a dimension of the key sequence $K_i$.

In sub-step 803-3, perform feature concatenation on output features of head structures in the $j^{th}$ layer of feature encoder to obtain a combined feature of the $j^{th}$ layer of feature encoder.

The feature concatenation may be performed by the concat( ) method to obtain the combined feature Z.

Expressed by a calculation formula: combined feature $Z = \mathrm{Concat}(head_1, \ldots head_m)W^O$, m being the quantity of the head structure.

In sub-step 803-4, perform linear transformation on the combined feature of the $j^{th}$ layer of feature encoder based on a fourth linear transformation matrix to obtain an output feature of the multi-head attention layer of the $j^{th}$ layer of feature encoder.

The fourth linear transformation matrix may be represented by symbol $W^O$. $W_i^Q$, $W_i^K$, $W_i^V$, and $W^O$ may be randomly initialized and obtained through training. This is not specifically limited in this embodiment of this disclosure.

In sub-step 803-5, input the output feature of the multi-head attention layer of the $j^{th}$ layer of feature encoder to the feedforward neural network layer of the $j^{th}$ layer of feature encoder, and determine an output of the feedforward neural network layer as an input feature of a $(j+1)^{th}$ layer of feature encoder.

For example, the feedforward neural network may perform two linear transformations and one nonlinear transformation on the output feature of the multi-head attention layer of the $j^{th}$ layer of feature encoder. This is not specifically limited in this embodiment of this disclosure.

The method for training a model provided in the embodiments of this disclosure is performed through step 801 to step 803. The following describes a method for applying the trained molecular property prediction network, that is, the method for determining a drug molecule property provided in the embodiments of this disclosure, performed through step 804 to step 806.

In step 804, obtain a text string of a to-be-tested drug molecule, the text string being used for describing a chemical structural formula of the to-be-tested drug molecule.

This step may be performed with reference to step 301.

In step 805, obtain a three-dimensional structure coordinate matrix, a normalized adjacency matrix, an atomic feature, and a chemical bond feature of the to-be-tested drug molecule according to the text string of the to-be-tested drug molecule; and perform feature concatenation on the three-dimensional structure coordinate matrix, the normalized adjacency matrix, the atomic feature, and the chemical bond feature of the to-be-tested drug molecule to obtain a first concatenated matrix.

This step may be performed with reference to step 302.

In step 806, input the first concatenated matrix of the to-be-tested drug molecule to the trained molecular property prediction network to obtain a predicted property value outputted from the molecular property prediction network, the predicted property value outputted being used for indicating the drug-forming property of the to-be-tested drug molecule.

This step may be performed with reference to step 303.

The method provided in the embodiments of this disclosure has at least the following beneficial effects:

According to an aspect, the three-dimensional structure information of a molecule is introduced, and a DA method based on the three-dimensional structure information of the molecule is provided, so that the accuracy of molecular property prediction is increased. According to another aspect, the Transformer model in the field of natural language processing is introduced, and a new method for applying the Transformer model in the field of molecular property prediction is provided, so that the accuracy of molecular property is further increased due to a powerful expressive capability of the Transformer model.

Based on the above, the three-dimensional structure information, the two-dimensional structure information, the atomic feature, and the chemical bond feature of the to-be-tested drug molecule are obtained, and the features are concatenated as input data of the Transformer model. This method greatly increases the accuracy of predicting the drug molecule property.

Figure 10:
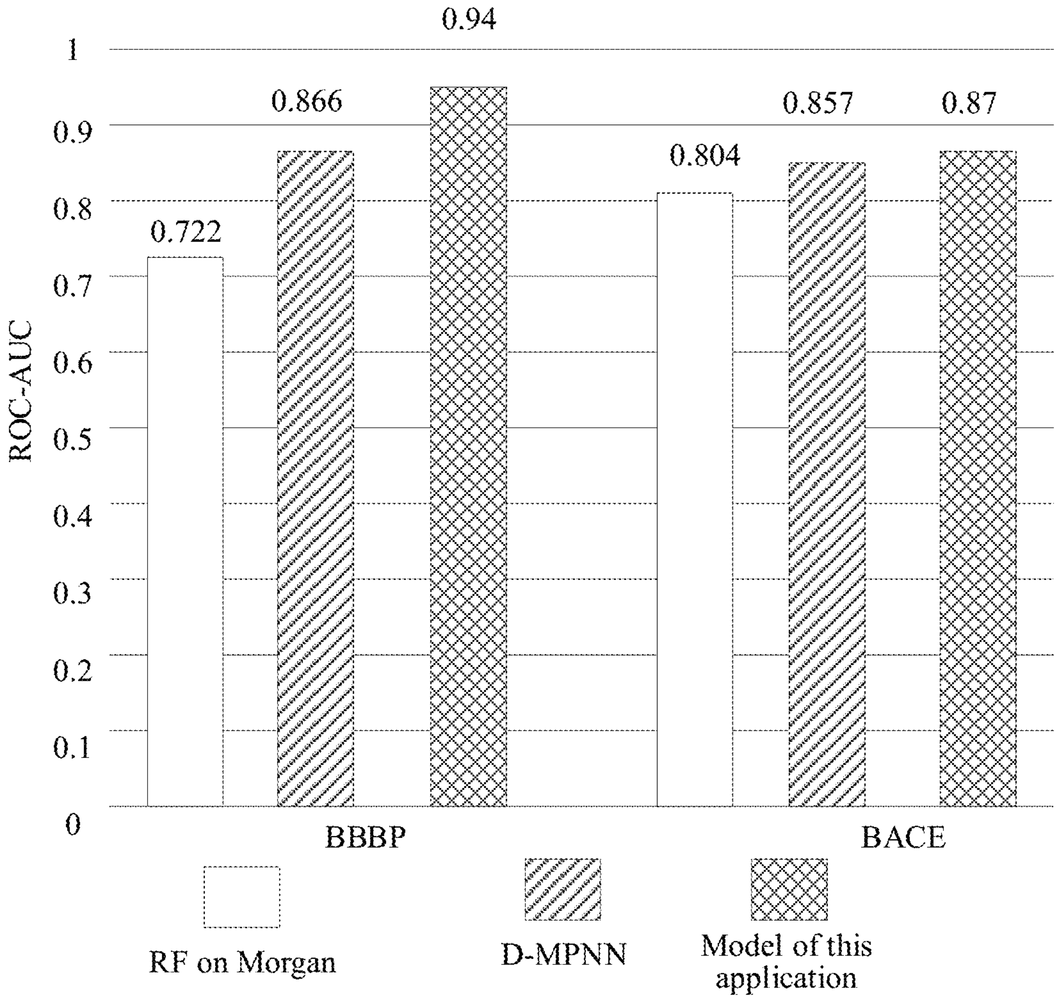
FIG. 10 is a schematic diagram of an experimental result according to an embodiment of this disclosure.
Figure 11:
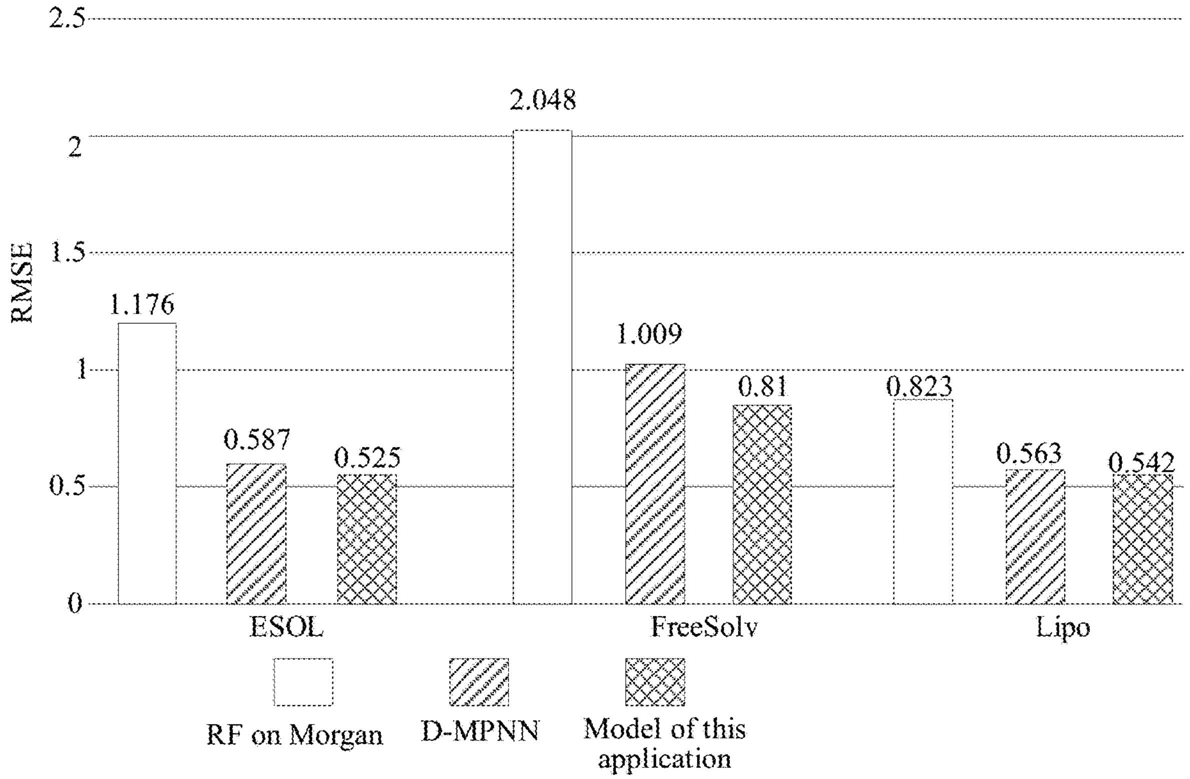
FIG. 11 is a schematic diagram of another experimental result according to an embodiment of this disclosure.

For example, the solution for predicting a drug molecule property provided in the embodiments of this disclosure is compared with the solution for predicting a drug molecule property provided in the related art by experiments based on the standard data set MoleculeNet to obtain the experimental results shown in FIG. 10 and FIG. 11.

A larger numerical value of receiver operating characteristic (ROC)-area under the curve (AUC) indicates a better result, and a smaller numerical value of root mean square error (RMSE) indicates a better result.

FIG. 10 shows experimental results of different prediction solutions in a classification data set. The data set is divided by the Scaffold method. Three different algorithms include the random forest algorithm based on Morgan molecular fingerprints (RF on Morgan), D-MPNN (graph neural network), and the solution for predicting a drug molecule property provided in the embodiments of this disclosure. It can be recognized that in two classification data sets, the solution for predicting a drug molecule property provided in the embodiments of this disclosure has a better experimental result than other prediction solutions. FIG. 11 shows experimental results of the three algorithms in a regression data set. Similarly, it can be recognized that the solution for predicting a drug molecule property provided in the embodiments of this disclosure has a better experimental result than other prediction solutions in three regression data sets.

In the embodiments of this disclosure, the DA method based on the three-dimensional structure information of the drug molecule is applied to the Transformer model. In an actual implementation process, the Transformer model may be replaced with another neural network model (for example, a graph neural network). Moreover, in addition to using the average pooling layer as an atomic information aggregator, in an actual implementation process, the average pooling layer may be replaced with a max pooling layer or an aggregator such as Set2Set. This is not specifically limited in this embodiment of this disclosure.

Figure 12:
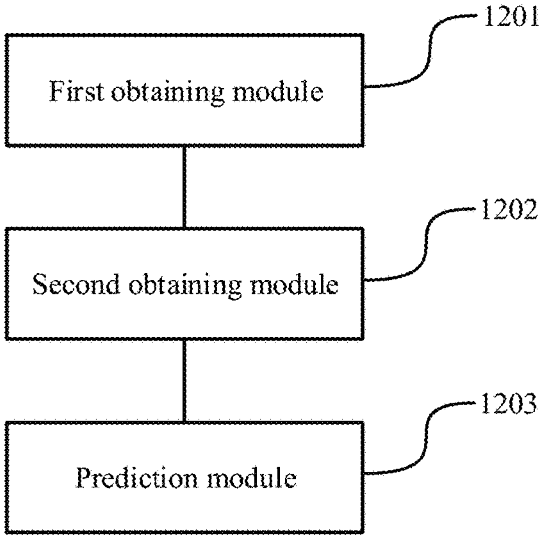
FIG. 12 is a schematic structural diagram of an apparatus for determining a drug molecule property according to an embodiment of this disclosure.

FIG. 12 is a schematic structural diagram of an apparatus for determining a drug molecule property according to an embodiment of this disclosure. One or more modules, submodules, and/or units of the apparatus can be implemented by processing circuitry, software, or a combination thereof, for example. Referring to FIG. 12, the apparatus for determining a drug molecule property includes: a first obtaining module 1201, a second obtaining module 1202, and a first prediction module 1203.

The first obtaining module 1201 is configured to obtain a text string of a to-be-tested drug molecule, the text string being used for describing a chemical structural formula of the to-be-tested drug molecule.

The second obtaining module 1202 is configured to obtain three-dimensional structure information of the to-be-tested drug molecule according to the text string.

The first prediction module 1203 is configured to determine a drug-forming property of the to-be-tested drug molecule according to the three-dimensional structure information.

In a possible implementation, the second obtaining module is further configured to obtain two-dimensional structure information of the to-be-tested drug molecule according to the text string.

The first prediction module is further configured to determine the drug-forming property of the to-be-tested drug molecule according to the three-dimensional structure information and the two-dimensional structure information.

In a possible implementation, the second obtaining module is further configured to obtain an atomic feature and a chemical bond feature of the to-be-tested drug molecule according to the text string.

The first prediction module is further configured to determine the drug-forming property of the to-be-tested drug molecule according to the three-dimensional structure information, the atomic feature and the chemical bond feature of the to-be-tested drug molecule.

In a possible implementation, the second obtaining module is further configured to obtain two-dimensional structure information of the to-be-tested drug molecule according to the text string; and obtain an atomic feature and a chemical bond feature of the to-be-tested drug molecule according to the text string.

The first prediction module is further configured to determine the drug-forming property of the to-be-tested drug molecule according to the three-dimensional structure information, the two-dimensional structure information, the atomic feature, and the chemical bond feature.

In a possible implementation, the first prediction module is further configured to determine the drug-forming property of the to-be-tested drug molecule according to the three-dimensional structure information through a Transformer model.

In a possible implementation, the second obtaining module includes a first obtaining unit and a first processing unit. The first obtaining unit is configured to obtain three-dimensional structure coordinates of the to-be-tested drug molecule according to the text string. The first processing unit is configured to perform transformation on the three-dimensional structure coordinates of the to-be-tested drug molecule when a three-dimensional structure shape of the to-be-tested drug molecule remains unchanged, to obtain a three-dimensional structure coordinate matrix as the three-dimensional structure information of the to-be-tested drug molecule.

In a possible implementation, the second obtaining module further includes: a second obtaining unit and a second obtaining unit. The second obtaining unit is configured to obtain an adjacency matrix corresponding to a two-dimensional structure diagram of the to-be-tested drug molecule according to the text string. The second processing unit is configured to perform normalization on the adjacency matrix corresponding to the two-dimensional structure diagram to obtain a normalized adjacency matrix as the two-dimensional structure information of the to-be-tested drug molecule.

In a possible implementation, the first prediction module is further configured to:

perform feature concatenation on the three-dimensional structure coordinate matrix, the normalized adjacency matrix, the atomic feature, and the chemical bond feature to obtain a first concatenated matrix; and determine a predicted property value according to the first concatenated matrix through a molecular property prediction network, the predicted property value being used for indicating the drug-forming property of the to-be-tested drug molecule.

In a possible implementation, the molecular property prediction network includes a feature encoding layer, a pooling layer, and a linear layer; and the first prediction module is further configured to:

input the first concatenated matrix to the feature encoding layer and the pooling layer sequentially; and input an encoded vector outputted from the pooling layer to the linear layer, and determine an output of the linear layer as the predicted property value of the to-be-tested drug molecule.

In a possible implementation, the first obtaining unit is configured to:

obtain the chemical structural formula of the to-be-tested drug molecule according to the text string;

determine M three-dimensional structures with different conformers according to the chemical structural formula of the to-be-tested drug molecule, a root mean squared error (RMSE) between two three-dimensional structures with different conformers being greater than a first threshold, and M being a positive integer greater than 1;

perform energy minimization on the M three-dimensional structures respectively under a target molecular force field;

determine a three-dimensional structure with a minimum energy from the M three-dimensional structures as a target three-dimensional structure;

remove a hydrogen atom from the target three-dimensional structure to obtain a three-dimensional structure of the to-be-tested drug molecule; and obtain three-dimensional coordinates of each atom in the to-be-tested drug molecule under the three-dimensional structure of the to-be-tested drug molecule to obtain the three-dimensional structure coordinates of the to-be-tested drug molecule.

In a possible implementation, the first processing unit is configured to:

obtain a random rotation matrix and a translation transformation matrix; and perform, when the three-dimensional structure shape of the to-be-tested drug molecule remains unchanged, random rotation and translation transformation on a three-dimensional structure of the to-be-tested drug molecule respectively according to the random rotation matrix and the translation transformation matrix to obtain the three-dimensional structure coordinate matrix, the three-dimensional structure coordinate matrix including new three-dimensional structure coordinates of the to-be-tested drug molecule.

In a possible implementation, the second processing unit is configured to:

transform a value of a diagonal element of the adjacency matrix from a first numerical value to a second numerical value to obtain a new adjacency matrix; and perform normalization on the new adjacency matrix to obtain the normalized adjacency matrix.

Figure 13:
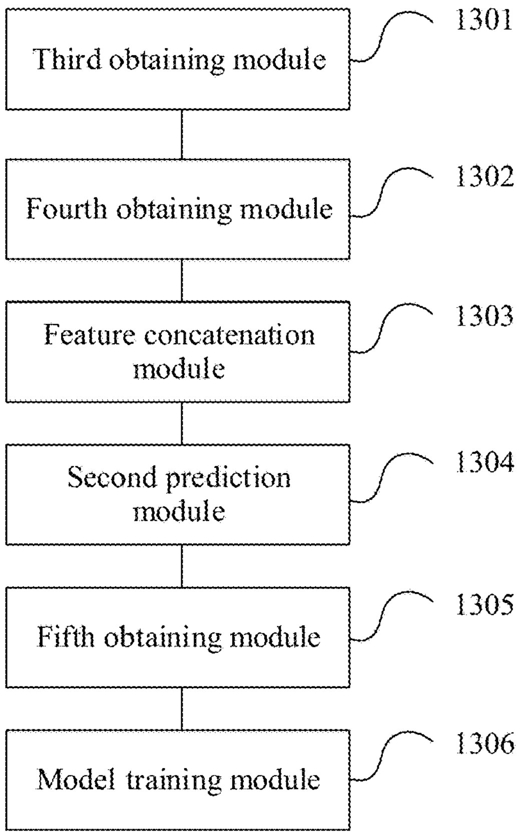
FIG. 13 is a schematic structural diagram of an apparatus for training a model according to an embodiment of this disclosure.

FIG. 13 is a schematic structural diagram of an apparatus for training a model according to an embodiment of this disclosure. One or more modules, submodules, and/or units of the apparatus can be implemented by processing circuitry, software, or a combination thereof, for example. Referring to FIG. 13, the apparatus for training a model includes a third obtaining module 1301, a fourth obtaining module 1302, a feature concatenation module 1303, a second prediction module 1304, a fifth obtaining module 1305, and a model training module 1306.

The third obtaining module 1301 is configured to obtain a training data set, the training data set including a sample molecule and a property label matching the sample molecule.

The fourth obtaining module 1302 is configured to obtain a three-dimensional structure coordinate matrix, a normalized adjacency matrix, an atomic feature, and a chemical bond feature of the sample molecule.

The feature concatenation module 1303 is configured to perform feature concatenation on the three-dimensional structure coordinate matrix, the normalized adjacency matrix, the atomic feature, and the chemical bond feature of the sample molecule to obtain a second concatenated matrix.

The second prediction module 1304 is configured to determine a predicted property value corresponding to the sample molecule according to the second concatenated matrix through an initial neural network.

The fifth obtaining module 1305 is configured to obtain a loss value between the predicted property value corresponding to the sample molecule and the property label of the sample molecule based on a target loss function.

The model training module 1306 is configured to iteratively update network parameters of the initial neural network in response to the loss value being greater than a second threshold until the loss value is not greater than the second threshold to obtain a molecular property prediction network.

In a possible implementation, the initial neural network includes a feature encoding layer, a pooling layer, and a linear layer; and the second prediction module is further configured to:

input the second concatenated matrix to the feature encoding layer and the pooling layer sequentially; and input an encoded vector outputted from the pooling layer to the linear layer, and determine an output of the linear layer as the predicted property value of the to-be-tested drug molecule.

In a possible implementation, the feature encoding layer includes N layers of feature encoders with the same structure that are sequentially stacked, N being a positive integer; and the second prediction module is further configured to:

input the second concatenated matrix as an input feature to a first layer of feature encoder of the feature encoding layer;

encode the input feature sequentially through the N layers of feature encoders stacked until a last layer of feature encoder, an output of a previous layer of feature encoder being used as an input of a next layer of feature encoder; and determine an output of the last layer of feature encoder as an output feature of the feature encoding layer.

In a possible implementation, each layer of feature encoder includes a multi-head attention layer and a feedforward neural network layer; and the second prediction module is further configured to:

obtain, when a $j^{th}$ layer of feature encoder includes an $i^{th}$ head structure of the multi-head attention layer, a first linear transformation matrix, a second linear transformation matrix, and a third linear transformation matrix corresponding to the $i^{th}$ head structure, both i and j being positive integers, $1 \leq j \leq N$;

perform linear transformation on an input feature of the $i^{th}$ head structure respectively according to the first linear transformation matrix, the second linear transformation matrix, and the third linear transformation matrix to obtain a query sequence, a key sequence, and a value sequence of the $i^{th}$ head structure sequentially; obtain an output feature of the $i^{th}$ head structure according to the query sequence, the key sequence, and the value sequence of the $i^{th}$ head structure;

perform feature concatenation on output features of head structures in the $j^{th}$ layer of feature encoder to obtain a combined feature of the $j^{th}$ layer of feature encoder;

perform linear transformation on the combined feature of the $j^{th}$ layer of feature encoder based on a fourth linear transformation matrix to obtain an output feature of the multi-head attention layer of the $j^{th}$ layer of feature encoder; and input the output feature of the multi-head attention layer of the $j^{th}$ layer of feature encoder to the feedforward neural network layer of the $j^{th}$ layer of feature encoder, and determine an output of the feedforward neural network layer as an input feature of a $(j+1)^{th}$ layer of feature encoder.

All the foregoing optional technical solutions may be combined in various manners to form other embodiments of this disclosure, and details are not described herein again.

The drug molecule property being predicted by the apparatus for determining a drug molecule property provided in the foregoing embodiments based on AI technology is illustrated with an example of division of the foregoing functional modules. In actual application, the functions may be allocated to and completed by different functional modules according to requirements, that is, the internal structure of the apparatus is divided into different functional modules, to implement all or some of the functions described above. In addition, the apparatus and method embodiments for determining a drug molecule property provided in the foregoing embodiments belong to the same concept. For the specific implementation process, reference may be made to the method embodiments, and details are not described herein again.

The term module (and other similar terms such as unit, submodule, etc.) in this disclosure may refer to a software module, a hardware module, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each module can be part of an overall module that includes the functionalities of the module.

Figure 14:
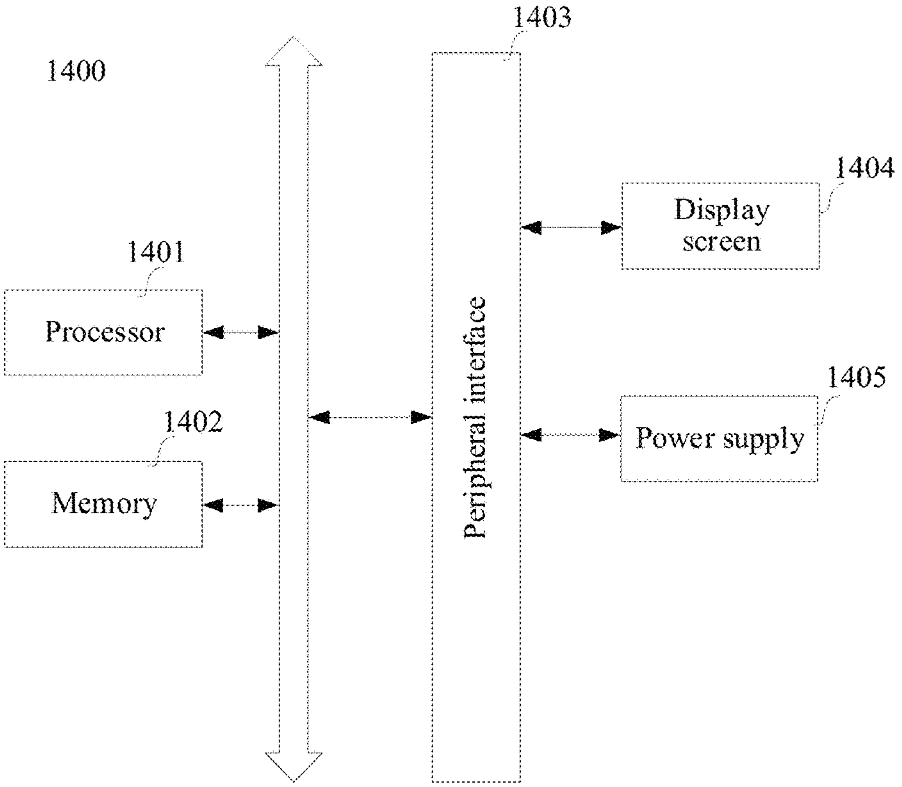
FIG. 14 is a schematic structural diagram of a computer device according to an embodiment of this disclosure.

FIG. 14 is a structural block diagram of a computer device 1400 according to an exemplary embodiment of this disclosure. Generally, the computer device 1400 includes a processor 1401 and a memory 1402.

Processing circuitry, such as the processor 1401, may include one or more processing cores, for example, a 4-core processor or an 8-core processor. The processor 1401 may be implemented in at least one hardware form of digital signal processing (DSP), field-programmable gate array (FPGA), and programmable logic array (PLA). The processor 1401 may also include a main processor and a coprocessor. The main processor is a processor for processing data in a wake-up state, also referred to as a central processing unit (CPU). The coprocessor is a low power consumption processor configured to process data in a standby state. In some embodiments, the processor 1401 may be integrated with a graphics processing unit (GPU). The GPU is configured to render and draw content that needs to be displayed on a display. In some embodiments, the processor 1401 may also include an artificial intelligence (AI) processor. The AI processor is configured to process a computing operation related to machine learning.

The memory 1402 may include one or more computer-readable storage media that may be non-transitory. The memory 1402 may also include a high-speed random-access memory and a non-volatile memory, such as one or more magnetic disk storage devices or a flash storage device. In some embodiments, a non-transitory computer-readable storage medium in the memory 1402 is configured to store at least one piece of program code, and the at least one piece of program code is used for being executed by the processor 1401 to implement the method for determining a drug molecule property provided in the method embodiments of this disclosure.

In some embodiments, the computer device 1400 further includes a peripheral interface 1403 and at least one peripheral. The processor 1401, the memory 1402, and the peripheral interface 1403 may be connected through a bus or a signal cable. Each peripheral may be connected to the peripheral interface 1403 through a bus, a signal cable, or a circuit board. Specifically, the peripheral includes a display screen 1404 and a power supply 1405.

A person skilled in the art may understand that the structure shown in FIG. 14 does not constitute any limitation on the computer device 1400, and the computer device may include more components or fewer components than those shown in the figure, or some components may be combined, or a different component deployment may be used.

In an exemplary embodiment, a computer-readable storage medium, for example, a memory including program code is further provided. The program code may be executed by a processor in a terminal to implement the method for determining a drug molecule property in the foregoing embodiments. For example, the computer-readable storage medium may be a read-only memory (ROM), a random-access memory (RAM), a compact disc read-only memory (CD-ROM), a magnetic tape, a floppy disk, an optical data storage device, and the like.

In an exemplary embodiment, a computer program product or a computer program is provided. The computer program product or the computer program includes computer program code, the computer program code being stored in a computer-readable storage medium, a processor of a computer device reading the computer program code from the computer-readable storage medium and executing the computer program code, to cause the computer device to implement the method for determining a drug molecule property as above.

What is claimed is:

1. A method for determining a drug molecule property, the method comprising:

obtaining a text string of a drug molecule, the text string indicating a structural formula of the drug molecule;

executing, by processing circuitry, a cheminformatics software tool to obtain three-dimensional structure coordinates, an atomic feature, and a chemical bond feature of the drug molecule based on the structural formula indicated by the text string;

performing transformation on the three-dimensional structure coordinates of the drug molecule while a shape of a three-dimensional structure of the drug molecule remains unchanged, to generate a three-dimensional structure coordinate matrix;

performing, by the processing circuitry, feature concatenation on at least the three-dimensional structure coordinate matrix, the atomic feature, and the chemical bond feature to generate a concatenated matrix;

determining, by the processing circuitry, a drug-forming property of the drug molecule based on the concatenated matrix through a molecular property prediction network model.

2. The method according to claim 1, further comprising:

generating two-dimensional structure information of the drug molecule based on the structural formula indicated by the text string, wherein the feature concatenation is performed further on the two-dimensional structure information such that the concatenated matrix incorporates the two-dimensional structure information.

3. The method according to claim 1, wherein the molecular property prediction network model includes a feature encoding layer, a pooling layer, and a linear layer; and the feature encoding layer is based on a transformer model or a graph neural network model.

4. The method according to claim 2, wherein the generating the two-dimensional structure information comprises:

generating an adjacency matrix corresponding to a two-dimensional structure diagram of the drug molecule according to the structural formula indicated by the text string; and performing normalization on the adjacency matrix corresponding to the two-dimensional structure diagram to generate a normalized adjacency matrix as the two-dimensional structure information of the drug molecule.

5. The method according to claim 1, wherein the determining the drug-forming property of the drug molecule comprises:

determining a predicted property value according to the concatenated matrix through the molecular property prediction network model, the predicted property value indicating the drug-forming property of the drug molecule.

6. The method according to claim 5, wherein the molecular property prediction network model includes a feature encoding layer, a pooling layer, and a linear layer; and the determining the predicted property value includes:

inputting the concatenated matrix to the feature encoding layer followed by the pooling layer; and inputting an encoded vector outputted from the pooling layer to the linear layer, an output of the linear layer being the predicted property value of the drug molecule.

7. The method according to claim 1, wherein the executing the cheminformatics software tool to obtain the three-dimensional structure coordinates comprises:

obtaining the structural formula of the drug molecule according to the text string;

determining M three-dimensional structures with different conformers according to the structural formula of the drug molecule, a root mean squared error (RMSE) between two three-dimensional structures with different conformers being greater than a first threshold, and M being a positive integer greater than 1;

performing energy minimization on the M three-dimensional structures respectively under a target molecular force field;

determining a three-dimensional structure with a minimum energy from the M three-dimensional structures as a target three-dimensional structure;

removing a hydrogen atom from the target three-dimensional structure to obtain a three-dimensional structure of the drug molecule; and obtaining respective sets of three-dimensional coordinates of each atom in the drug molecule under the three-dimensional structure of the drug molecule to obtain the three-dimensional structure coordinates of the drug molecule.

8. The method according to claim 1, wherein the performing the transformation comprises:

obtaining a random rotation matrix or a random translation matrix; and performing, while the shape of the three-dimensional structure of the drug molecule remains-unchanged, a rotation transformation or a translation transformation on a three-dimensional structure of the drug molecule respectively according to the random rotation matrix or the random translation matrix to obtain the three-dimensional structure coordinate matrix, the three-dimensional structure coordinate matrix including new three-dimensional structure coordinates of the drug molecule.

9. The method according to claim 4, wherein the performing the normalization comprises:
transforming a value of a diagonal element of the adjacency matrix from a first numerical value to a second numerical value to obtain a new adjacency matrix; and
performing normalization on the new adjacency matrix to obtain the normalized adjacency matrix.

10. A method for training a model, the method comprising:
obtaining a training data set, the training data set including a text string of a sample molecule and a property label associated with the sample molecule, the text string indicating a structural formula of the sample molecule;
executing, by processing circuitry, a cheminformatics software tool to obtain three-dimensional structure coordinates, an atomic feature, and a chemical bond feature of the sample molecule based on the structural formula indicated by the text string;
performing transformation on the three-dimensional structure coordinates of the sample molecule while a shape of a three-dimensional structure of the sample molecule remains unchanged, to generate a three-dimensional structure coordinate matrix;
generating an adjacency matrix corresponding to a two-dimensional structure diagram of the sample molecule according to the structural formula indicated by the text string;
performing normalization on the adjacency matrix corresponding to the two-dimensional structure diagram to generate a normalized adjacency matrix of the sample molecule;
performing, by the processing circuitry, feature concatenation on the three-dimensional structure coordinate matrix, the normalized adjacency matrix, the atomic feature, and the chemical bond feature of the sample molecule to generate a concatenated matrix;
determining, by the processing circuitry, a predicted property value corresponding to the sample molecule according to the concatenated matrix through an initial neural network model;
determining a loss value between the predicted property value corresponding to the sample molecule and the property label of the sample molecule based on a target loss function; and
iteratively updating, by the processing circuitry, network parameters of the initial neural network model in response to the loss value being greater than a threshold until the loss value is not greater than the threshold to obtain a molecular property prediction network model.

11. The method according to claim 10, wherein
the initial neural network model includes a feature encoding layer, a pooling layer, and a linear layer; and
the determining the predicted property value includes:
inputting the concatenated matrix to the feature encoding layer followed by the pooling layer; and
inputting an encoded vector outputted from the pooling layer to the linear layer, an output of the linear layer being the predicted property value of the sample molecule.

12. The method according to claim 11, wherein
the feature encoding layer includes N layers of feature encoders with a same structure that are sequentially stacked, N being a positive integer; and
the method further includes:
inputting the concatenated matrix as an input feature to a first layer of feature encoder of the feature encoding layer;
encoding the input feature sequentially through the N layers of feature encoders stacked until a last layer of feature encoder, an output of a previous layer of feature encoder being used as an input of a next layer of feature encoder; and
determining an output of the last layer of feature encoder as an output feature of the feature encoding layer.

13. The method according to claim 12, wherein
each layer of feature encoder includes a multi-head attention layer and a feedforward neural network layer; and
the encoding the input feature sequentially through the N layers of feature encoders stacked includes:
obtaining, when a $j^{th}$ layer of feature encoder includes an $i^{th}$ head structure of the multi-head attention layer, a first linear transformation matrix, a second linear transformation matrix, and a third linear transformation matrix corresponding to the $i^{th}$ head structure, both i and j being positive integers, $1 \leq j \leq N$;
performing linear transformation on an input feature of the $i^{th}$ head structure respectively according to the first linear transformation matrix, the second linear transformation matrix, and the third linear transformation matrix to obtain a query sequence, a key sequence, and a value sequence of the $i^{th}$ head structure sequentially;
obtaining an output feature of the $i^{th}$ head structure according to the query sequence, the key sequence, and the value sequence of the $i^{th}$ head structure;
performing feature concatenation on output features of head structures in the $j^{th}$ layer of feature encoder to obtain a combined feature of the $j^{th}$ layer of feature encoder;
performing linear transformation on the combined feature of the $j^{th}$ layer of feature encoder based on a fourth linear transformation matrix to obtain an output feature of the multi-head attention layer of the $j^{th}$ layer of feature encoder;
inputting the output feature of the multi-head attention layer of the $j^{th}$ layer of feature encoder to the feedforward neural network layer of the $j^{th}$ layer of feature encoder, and
determining an output of the feedforward neural network layer as an input feature of a $(j+1)^{th}$ layer of feature encoder.

14. An apparatus, comprising:
processing circuitry configured to:
obtain a text string of a drug molecule, the text string indicating a structural formula of the drug molecule;
execute a cheminformatics software tool to obtain at least three-dimensional structure coordinates, an atomic feature, and a chemical bond feature of the drug molecule based on the structural formula indicated by the text string;
perform transformation on the three-dimensional structure coordinates of the drug molecule while a shape of a three-dimensional structure of the drug molecule remains unchanged, to generate a three-dimensional structure coordinate matrix;

perform feature concatenation on at least the three-dimensional structure coordinate matrix, the atomic feature, and the chemical bond feature to generate a concatenated matrix; and determine a drug-forming property of the drug molecule based on the concatenated matrix through a molecular property prediction network model.

15. A non-transitory computer-readable storage medium storing instructions which when executed by a computer cause the computer to perform the method according to claim 1.

16. A non-transitory computer-readable storage medium storing instructions which when executed by a processor cause the processor to perform the method according to claim 10.

17. The apparatus according to claim 14, wherein the processing circuitry is configured to:

generate two-dimensional structure information of the drug molecule based on the structural formula indicated by the text string, wherein the feature concatenation is performed further on the two-dimensional structure information such that the concatenated matrix incorporates the two-dimensional structure information.

18. The apparatus according to claim 17, wherein the processing circuitry is configured to:

generate an adjacency matrix corresponding to a two-dimensional structure diagram of the drug molecule according to the structural formula indicated by the text string; and perform normalization on the adjacency matrix corresponding to the two-dimensional structure diagram to generate a normalized adjacency matrix as the two-dimensional structure information of the drug molecule.

19. The apparatus according to claim 14, wherein the molecular property prediction network model includes a feature encoding layer, a pooling layer, and a linear layer; and the feature encoding layer is based on a transformer model or a graph neural network model.

20. The apparatus according to claim 14, wherein the processing circuitry is configured to:

determine a predicted property value according to the concatenated matrix through the molecular property prediction network model, the predicted property value indicating the drug-forming property of the drug molecule.

* * * * *